United States Patent [19]

Southern, Jr. et al.

[11] Patent Number: 5,336,672
[45] Date of Patent: Aug. 9, 1994

[54] INCREASING EGG PRODUCTION IN POULTRY

[75] Inventors: Lincoln L. Southern, Jr., Denham Springs; Timothy G. Page, Walker, both of La.

[73] Assignee: Board of Supervisors of Louisiana State University and Agricultural and Mechanical College, Baton Rouge, La.

[21] Appl. No.: 917,766

[22] Filed: Jul. 21, 1992

[51] Int. Cl.⁵ .................... A61K 31/555; A61K 31/28
[52] U.S. Cl. ..................................... 514/188; 514/505
[58] Field of Search .................. 514/505, 188; 424/655

[56] References Cited

U.S. PATENT DOCUMENTS 4,315,927  2/1982  Evans ................................. 514/188
5,087,624  2/1992  Boynton et al. ..................... 514/188

FOREIGN PATENT DOCUMENTS 88105246  9/1988  China .

OTHER PUBLICATIONS

Chemical Abstracts (111:231193s) 1989; CN 88,105,246, 28 Sep. 1988.
National Research Council, "Nutrient Requirements of Poultry," pp. 7, 12, 13, 17, 19, 20, 21, 22 (1984).
Jensen et al., "Evidence for a New Biological Function of Chromium," Fed. Proc. vol. 37, p. 1015 (1978).
Polansky et al., "Chromium, Copper, Iron, Manganese and Zinc Concentrations of Tissues from Turkey Hens: Effects of Egg Production and Supplemental Chromium," FASEB Journal vol. 3, p. A1072 (1989).
Steele et al., "Trivalent Chromium and Nicotinic Acid Supplementation for the Turkey Poult," Poult. Sci. vol. 58, pp. 983–984 (1979).
Rosebrough et al., "Effect of Supplemental Dietary Chromium or Nicotinic Acid on Carbohydrate Metabolism During Basal, Starvation, and Refeeding Periods in Poults," Poult. Sci. vol. 60 pp. 407–417 (1981).
Anderson et al., "Chromium Supplementation of Turkeys: Effects on Tissue Chromium," J. Agri. Food. Chem. vol. 37, pp. 131–134 (1989).
Jensen et al., "Dietary Chromium and Interior Egg Quality," Poult. Sci. vol. 59, pp. 341–346 (1980).
Riales et al., "Effect of Chromium Chloride Supplementation on Glucose Tolerance and Serum Lipids Including High-density Lipoproteins of Adult Men," Am. J. Clin. Nutr. vol. 34, pp. 2670–2678 (1981).
Abraham et al., "The Effect of Chromium on Established Atherosclerotic Plaques in Rabbits," Am. J. Clin. Nutr. vol. 33, pp. 2294–2298 (1980).
Evans et al., "Growth Stimulating Effect of Picolinic Acid Added to Rat Diets," Proc. Soc. Exp. Biol. & Med., vol. 165, pp. 457–461 (1980).
Hill et al., "Zinc–Amino Acid Complexes for Swine," J. Anim. Sci., vol. 63, pp. 121–130 (1986).

Primary Examiner—Marianne M. Cintins
Assistant Examiner—K. Weddington
Attorney, Agent, or Firm—John H. Runnels

[57] ABSTRACT

Egg production in poultry can be increased by the administration of chromium picolinate, preferably as a feed additive. The amounts of chromium picolinate required are low, so this method of increasing egg production can be administered both easily and economically.

12 Claims, No Drawings

INCREASING EGG PRODUCTION IN POULTRY

This invention pertains to increasing egg production in poultry, particularly to increasing egg production through the administration of chromium picolinate.

The desirability of an easy-to-implement means of increasing egg production in poultry requires no citation.

The National Research Council has listed no dietary chromium (Cr) requirement for poultry, although possible use as a trace element is mentioned. "Nutrient Requirements of Poultry," National Research Council, pp. 7, 12, 13, 17, 19, 20, 21, 22 (1984). Jensen et al., "Evidence for a New Biological Function of Chromium," Fed. Proc. Vol. 37, p 1015 (1978), stated that Cr was biologically active in the laying hen. Polansky et al., "Chromium, Copper, Iron, Manganese and Zinc Concentrations of Tissues from Turkey Hens: Effects of Egg Production and Supplemental Chromium," FASEB Journal Vol. 3, p A1072 (1989) indicated decreases in tissue Cr during turkey egg production. The growth rate of turkey poults has been reported to be improved by Cr, and it has been suggested that this effect may depend on the presence of Cr (III) in an organic form. Steele et at., "Trivalent Chromium and Nicotinic Acid Supplementation for the Turkey Poult," Poult. Sci. Vol. 58, pp. 983-84 (1979); Rosebrough et al., "Effect of Supplemental Dietary Chromium or Nicotinic Acid on Carbohydrate Metabolism During Basal, Starvation, and Refeeding Periods in Poults," Poult. Sci. Vol. 60 pp. 407-17 (1981). Supplemental Cr has been reported to produce a small increase in turkey breast tissue. Anderson et al., "Chromium Supplementation of Turkeys: Effects on Tissue Chromium," J. Agri. Food. Chem. Vol. 37, pp. 131-134 (1989). Jensen et al., "Dietary Chromium and Interior Egg Quality," Poult. Sci. Vol. 59, pp 341–46 (1980) evaluated the effect of $CrCl_3.6H_2O$ on egg production, but reported no positive effect.

Chromium has been linked to lipid metabolism. Studies have shown that Cr supplementation decreases serum triglycerides, and increases HDL cholesterol in adult men. Riales et al., "Effect of Chromium Chloride Supplementation on Glucose Tolerance and Serum Lipids Including High-density Lipoproteins of Adult Men," Am. J. Clin. Nutr. Vol. 34, pp. 2670-78 (1981). Abraham et al., "The Effect of Chromium on Established Atherosclerotic Plaques in Rabbits," Am. I. Clin. Nutr. Vol. 33, pp. 2294–98 (1980) reported that Cr decreased cholesterol (CH) accumulation in rabbits, and increased the removal rate of CH already deposited in the aorta.

Other studies have discussed effects of dietary picolinic acid. Evans et al., "Growth Stimulating Effect of Picolinic Acid Added to Rat Diets," Proc. Soc. Exp. Biol. & Med., vol. 165, pp. 457–61 (1980), reported greater growth rates in rats fed 200 mg/kg picolinic acid in their diet. The increased growth rates were attributed to increased zinc absorption. Hill et al., "Zinc-Amino Acid Complexes for Swine," J. Anita. Sci., vol. 63, pp. 121-30 (1986), on the other hand, concluded that picolinic acid did not aid zinc absorption, although it was reported to result in faster growth rates. It has been suggested that metals in the form of metal picolinates may be more available biologically for absorption. Evans, U.S. Pat. No. 4,315,927 (1982). This reference mentions chromium picolinate; but gives no physiological data related to chromium picolinate.

No prior reference suggests that the administration of chromium picolinate; (CrPic) would be expected to have any effect on egg production in poultry.

It has been discovered, quite unexpectedly, that administering chromium picolinate can increase the level of egg production in poultry. The original purpose of the study which led to this discovery was to investigate the effect of CrPic on egg cholesterol, egg fat, and egg protein. A completely unanticipated result was observed in laying hen egg production. Egg production was incrementally increased in some circumstances by supplementing the diet with CrPic. This supplementation is economical and easy to administer. We presently have no explanation for the mechanism underlying this increase in egg production.

The diet of poultry is advantageously supplemented with chromium picolinate in physiologically effective amounts. Chromium picolinate is the chromium (III) salt or coordination complex of picolinic acid (pyridine-2-carboxylic acid). The chromium picolinate used in the examples reported below was obtained from Nutrition 21 (San Diego, Calif.). Its synthesis is also described in Evans, U.S. Pat. No. 4,315,927, which is incorporated by reference.

While oral administration of chromium picolinate is generally preferred because of its simplicity, chromium picolinate could also be injected into the bloodstream, into muscle or fat tissue, or directly into the gastrointestinal tract, or administered as an implant. When administered orally, it will generally be incorporated into food material or drinking water. Alternatively, it could be incorporated into tablets, capsules, or pills along with one or more suitable diluents or carriers using known techniques. The generally preferred route of administration is by incorporation of chromium picolinate into a food material.

EXAMPLE 1

Hyline 36 commercial-type laying hens were taken from the Louisiana State University Agricultural Center Poultry Unit. The hens were 32–36 weeks of age during the 28 days of the trial. A randomized complete block design was used, and the hens were blocked on location in the barn. Hens were penned individually in cages (0.30×0.41 m) in an open front building. Each of the six treatments described below was replicated ten times, with one hen per replicate. The hens were fed a corn-soybean meal laying hen basal diet for one week. The composition of the diet is set forth in Table 1, and was formulated to meet or exceed the requirements for all nutrients as stated in "Nutrient Requirements of Poultry," National Research Council (1984). The hens were then randomly allotted to a treatment, and were fed the experimental diets during a 28-day trial. The following treatments were used: (1) Corn-soybean meal basal (B), (2) B+50 ppb Cr, (3) B+100 ppb Cr, (4) B+200 ppb Cr, (5) B+400 ppb Cr, and (6) B+800 ppb Cr. Cromium was administered as chromium picolinate. Treatment diets and water were provided on an ad libitum basis.

TABLE 1

| COMPOSITION OF THE BASAL DIET | |
|---|---|
| Ingredient | Percent by Weight |
| Corn | 60.0 |
| Soybean meal, | 25.0 |

TABLE 1-continued

| COMPOSITION OF THE BASAL DIET | |
|---|---|
| Ingredient | Percent by Weight |
| 44% Crude Protein | |
| Tallow | 5.0 |
| Dicalcium phosphate | 2.5 |
| Oyster shell flour | 7.0 |
| Salt | 0.25 |
| Vitamin and mineral premix[a] | 0.25 |

[a]Supplied per kg of diet: 11,000 IU vitamin A, 1650 ICU vitamin $D_3$, 8.25 IU vitamin E, 0.73 mg menadione sodium bisulfite, 1 mg thiamine, 4.4 mg riboflavin, 33 mg niacin, 8.1 mg d-pantothenic acid, 0.45 mg folic acid, 0.05 mg biotin, 2.2 mg pyridoxine, 0.01 mg vitamin $B_{12}$, 400 mg choline, 60 mg Mn, 44 mg Zn, 20 mg Fe, 2 mg Cu, 1.2 mg I, 0.20 mg Co.

Egg production was recorded daily, and eggs were collected on Days 2, 9, 16, and 23 for determination of specific gravity [weight in air/(weight in air−weight in water)] and Haugh units. (Haugh unit=100 $Log_{10}$ (Albumen height (in mm)+(7.57−(1.7) (Egg mass in grams)$^{037}$))). Eggs were collected on Days 0, 7, 14, 21, and 28 for CH analysis. To determine yolk CH, eggs were hard-cooked by immersion in boiling water for 5 min. Yolks were removed and weighed. The entire yolk was blended with a volume of isopropyl alcohol proportional to the yolk weight (10 ml/g of yolk). The cholesterol content of this extract (mg per g wet weight) was determined by an automated procedure based on the Lieberman-Burchard method. One egg was collected on Day 22 for determination of percentage of egg fat using the acid hydrolysis method, and one egg was collected on Day 24 for determination of percentage of egg crude protein by the Kjeldahl N method. Data were analyzed by analysis of variance. Linear, quadratic, and cubic contrasts were used to evaluate the treatment effects. Egg production, specific gravity, Haugh units, and CH were measured over time and analyzed by split-plot analyses using hen(trt*rep) as the error term in the model.

Results are given in Table 2. Egg production was increased (Cr cubic, $P<0.03$) by CrPic through 200 ppb Cr, and decreased at 400 and 800 ppb Cr. Egg CH was not affected ($P>0.1$) by CrPic supplementation; however, CH tended to be lower in eggs from hens receiving 100 and 200 ppb Cr. By Day 28 of the trial, egg CH was reduced (Cr quadratic, $P<0.05$) by CrPic supplementation to the diet. Haugh units and specific gravity were not affected ($P>0.1$) by CrPic. Percentage of egg fat was higher in eggs from hens receiving 100 and 200 ppb Cr and lower in eggs from hens receiving 50, 400, and 800 ppb Cr (Cr quadratic, $P<0.1$). Percentage of egg crude protein was reduced (Cr quadratic, $P<0.02$) by CrPic supplementation to the diet.

TABLE 2

EFFECT OF CHROMIUM PICOLINATE ON EGG PRODUCTION, EGG CHOLESTEROL AND EGG QUALITY OF LAYING HENS[a], Example 1

| Item | Basal (B) | B + 50 ppb Cr | B + 100 ppb Cr | B + 200 ppb Cr | B + 400 ppb Cr | B + 800 ppb Cr | SEM[e] |
|---|---|---|---|---|---|---|---|
| Egg Production (%)[b] | 75.8 | 79.3 | 81.1 | 83.2 | 76.1 | 77.7 | 2.7 |
| Haugh units | 82.5 | 82.6 | 84.6 | 82.0 | 85.0 | 79.7 | 1.8 |
| Specific gravity | 1.086 | 1.085 | 1.084 | 1.084 | 1.084 | 1.085 | .001 |
| Egg fat (%)[c] | 10.4 | 10.2 | 10.6 | 10.8 | 10.0 | 9.9 | .2 |
| Egg Protein (%)[d] | 12.7 | 12.2 | 12.2 | 12.2 | 12.6 | 12.3 | .2 |
| Egg CH mg/g yolk | 12.1 | 12.1 | 11.7 | 11.9 | 12.1 | 11.9 | .2 |

[a]Data are means of 10 replicates of one hen each except for egg cholesterol, Haugh units, and specific gravity. Egg cholesterol is the mean of eggs from 10 replicates collected on Days 0, 7, 14, 21, and 28. Haugh units and specific gravity are the means of eggs from 10 replicates collected on Days 2, 9, 16, and 23. The experimental period was 28 days. Chromium was provided as chromium picolinate.
[b]Chromium cubic effect, $P < .03$.
[c]Chromium quadratic effect, $P < .10$.
[d]Chromium quadratic effect, $P < .02$.
[e]Standard Error of the Mean

EXAMPLE 2

The procedures described in Example 1 were followed, except as noted. The trial lasted eight weeks, and the hens were 28-36 weeks of age during the eight weeks of the trial. The treatments used were (1) Basal (B), (2) B+100 ppb Cr, (3) B+200 ppb Cr, (4) B+300 ppb Cr, and (5) B+400 ppb Cr. Only egg production is reported. The results are given in Table 3.

TABLE 3

EFFECT OF CHROMIUM PICOLINATE ON EGG PRODUCTION OF LAYING HENS, Example 2

| | Basal (B) | B + 100 ppb Cr | B + 200 ppb Cr | B + 300 ppb Cr | B + 400 ppb Cr | SEM |
|---|---|---|---|---|---|---|
| Egg Production (%) | 83.2 | 85.2 | 82.3 | 84.5 | 81.6 | 2.7 |

Chromium picolinate was not observed to affect egg production in this trial ($P>0.10$). However, a numerical increase in egg production at 100 ppb Cr was noted.

EXAMPLE 3

The procedures of Example 2 were followed, except that the hens were 48-56 weeks of age during the eight weeks of the trial. The results are given in Table 4.

TABLE 4

EFFECT OF CHROMIUM PICOLINATE ON EGG PRODUCTION OF LAYING HENS, Example 3

| | Basal (B) | B + 100 ppb Cr | B + 200 ppb Cr | B + 300 ppb Cr | B + 400 ppb Cr | SEM |
|---|---|---|---|---|---|---|
| Egg Production | 82.0 | 83.0 | 82.1 | 74.8 | 77.1 | 4.3 |

TABLE 4-continued

| EFFECT OF CHROMIUM PICOLINATE ON EGG PRODUCTION OF LAYING HENS, Example 3 | | | | | |
| --- | --- | --- | --- | --- | --- |
| Basal (B) | B + 100 ppb Cr | B + 200 ppb Cr | B + 300 ppb Cr | B + 400 ppb Cr | SEM |
| tion (%) | | | | | |

Chromium picolinate was not observed to affect egg production in this trial (P>0.10). However, a numerical increase in egg production at 100 ppb Cr was noted. Further, large-scale trials are planned to study further the significance of CrPic additions to laying hen diets.

Current laying hen diets are primarily composed of ingredients of plant origin, which are generally low in Cr. In view of the results reported here, it may be the case that existing laying hen diets may generally be too low in Cr for optimal hen productivity. Adequate absorption and utilization of Cr may be dependent on its association with an organic molecule. Picolinate, a tryptophan metabolite, is an effective chelator of some metals, including Cr(III). It may therefore increase the absorption or utilization of Cr.

Low effective dosages of CrPic are possible in implementations of the present invention. The results reported above suggest that them is an optimum dosage of CrPic, above which the level of egg production will decrease. The optimum dosage of CrPic found in the experiments reported above was in the neighborhood of 100–200 ppb Cr in the diet; but the optimal dosage may vary in individual circumstances, depending on factors such as the bird's age and the composition of the rest of the bird's diet. Determining the optimal dosage of CrPic in any particular set of circumstances will be a straightforward matter, following procedures such as described above.

We claim:

1. A method of increasing egg production in a laying bird, comprising the administration of chromium picolinate to the bird in an amount sufficient to increase the average level of egg production.

2. A method as recited in claim 1, wherein said chromium picolinate is administered in an aqueous solution.

3. A method as recited in claim 1, wherein said chromium picolinate is administered in combination with a food material suitable for consumption by a bird.

4. A method as recited in claim 3, wherein the ratio of the weight of the chromium to the weight of the food material is between 50 parts per billion and 400 parts per billion.

5. A method as recited in claim 4, wherein the ratio of the weight of the chromium to the weight of the food material is between 50 parts per billion and 200 parts per billion.

6. A method as recited in claim 4, wherein the ratio of the weight of the chromium to the weight of the food material is between 100 parts per billion and 200 parts per billion.

7. A method as recited in claim 1, wherein said bird is a chicken.

8. A method as recited in claim 2, wherein said bird is a chicken.

9. A method as recited in claim 3, wherein said bird is a chicken, and wherein said food material is suitable for consumption by a chicken.

10. A method as recited in claim 4, wherein said bird is a chicken, and wherein said food material is suitable for consumption by a chicken.

11. A method as recited in claim 5, wherein said bird is a chicken, and wherein said food material is suitable for consumption by a chicken.

12. A method as recited in claim 6, wherein said bird is a chicken, and wherein said food material is suitable for consumption by a chicken.

* * * * *